United States Patent
Hsieh et al.

(10) Patent No.: US 10,473,591 B2
(45) Date of Patent: Nov. 12, 2019

(54) HIGH THROUGHPUT METHOD AND APPARATUS FOR MEASURING MULTIPLE OPTICAL PROPERTIES OF A LIQUID SAMPLE

(71) Applicant: Wyatt Technology Corporation, Goleta, CA (US)

(72) Inventors: Vincent Hsieh, Santa Barbara, CA (US); Mario Yasa, Jr., Santa Barbara, CA (US); Steven C Minne, Santa Barbara, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

(21) Appl. No.: 15/583,899

(22) Filed: May 1, 2017

(65) Prior Publication Data

US 2018/0313758 A1   Nov. 1, 2018

(51) Int. Cl.
*G01N 21/64* (2006.01)
*G01N 21/51* (2006.01)
*G01N 21/47* (2006.01)

(52) U.S. Cl.
CPC ....... *G01N 21/6452* (2013.01); *G01N 21/474* (2013.01); *G01N 21/51* (2013.01);
(Continued)

(58) Field of Classification Search
CPC ............. G01N 21/6452; G01N 21/51; G01N 2021/6484; G01N 21/253; G01N 21/0303;
(Continued)

(56) References Cited

U.S. PATENT DOCUMENTS 4,343,991 A * 8/1982 Fujiwara ............ G01D 5/34723
250/227.11
4,431,307 A * 2/1984 Suovaniemi ........... G01N 21/03
356/246
(Continued)

FOREIGN PATENT DOCUMENTS

EP      0867710 A1    9/1998

OTHER PUBLICATIONS http://www.soft-matter.uni-tuebingen.de/index.html?dls.html.*
https://en.wikipedia.org/wiki/Fresnel_equations.*

*Primary Examiner* — Mohamed K Amara
(74) *Attorney, Agent, or Firm* — Leonard T. Guzman

(57) ABSTRACT

An apparatus for the high throughput measurement of optical properties of liquid samples placed into the wells of a multiwell plate is disclosed. An optical fiber within a fiber bundle containing no corrective optics between the fiber ends and the well plate bottom illuminates the sample in order to induce fluorescence, and multiple fibers collect emission radiation and transmit it to a fluorescence detector such as a spectrometer. Other embodiments involve a light scattering illumination source with detection fibers located in either the same bundle containing the fluorescence monitoring fibers or an independent light scattering detection bundle for the measurement of static and/or dynamic light scattering. Some embodiments of the invention permit the measurement of phase analysis light scattering. Thus the measurement of multiple optical properties of a liquid sample may be made simultaneously or in succession. A method for these measurements is also disclosed.

10 Claims, 5 Drawing Sheets

(52) U.S. Cl.
CPC .............. *G01N 2021/475* (2013.01); *G01N 2021/4747* (2013.01); *G01N 2021/6484* (2013.01); *G01N 2201/0833* (2013.01)

(58) Field of Classification Search
CPC .. G01N 21/7743; G01N 21/64; G01N 21/645; G01N 21/01; G01N 21/03; G01N 2201/06113; G01N 2021/513; G01N 2021/6491; G01N 21/532; G01N 30/02; G01N 15/0205; G01N 2021/0346; G01N 2021/6421; B01L 2300/0829; B01L 3/5085; B01L 2300/0654; B01L 2300/0851; B01L 2300/0819; G01J 3/02; G01J 3/0218; G01J 3/4406; G01J 3/2803; G01J 3/42; G01J 3/44
See application file for complete search history.

(56) References Cited

U.S. PATENT DOCUMENTS

| | | | | |
|---|---|---|---|---|
| 4,626,684 | A * | 12/1986 | Landa | G01N 21/6452 250/328 |
| 4,678,326 | A * | 7/1987 | Harjunmaa | G01N 21/255 250/227.11 |
| 4,722,606 | A * | 2/1988 | Bonfiglio | G01N 21/255 356/414 |
| 4,810,096 | A | 3/1989 | Russell | |
| 5,075,077 | A * | 12/1991 | Durley, III | B01L 3/545 422/424 |
| 5,169,601 | A * | 12/1992 | Ohta | B01L 3/5085 356/440 |
| 5,216,488 | A * | 6/1993 | Tguunanen | G01N 21/253 250/576 |
| 5,402,508 | A * | 3/1995 | O'Rourke | G01N 21/255 250/227.11 |
| 5,473,437 | A * | 12/1995 | Blumenfeld | G01N 21/253 356/417 |
| 5,518,923 | A * | 5/1996 | Berndt | G01N 21/253 356/319 |
| 5,774,610 | A * | 6/1998 | O'Rourke | G01N 21/8507 385/52 |
| 5,815,611 | A * | 9/1998 | Dhadwal | B82Y 15/00 385/12 |
| 6,024,920 | A * | 2/2000 | Cunanan | G01N 21/253 356/432 |
| 6,043,880 | A * | 3/2000 | Andrews | G01N 21/64 250/361 C |
| 6,124,937 | A * | 9/2000 | Mittenzwey | G01N 21/031 356/319 |
| 6,166,804 | A | 12/2000 | Potyrailo | |
| 6,222,970 | B1 * | 4/2001 | Wach | A61B 5/14546 385/115 |
| 6,316,774 | B1 | 11/2001 | Giebeler | |
| 6,377,842 | B1 | 4/2002 | Pogue | |
| 6,519,032 | B1 * | 2/2003 | Kuebler | B01D 15/08 356/246 |
| 6,576,476 | B1 * | 6/2003 | Taylor | G01N 21/253 422/52 |
| 6,597,450 | B1 * | 7/2003 | Andrews | G01N 21/64 356/246 |
| 6,630,108 | B1 * | 10/2003 | Randrianarivo | G01N 21/253 356/432 |
| 6,982,431 | B2 * | 1/2006 | Modlin | G01N 21/253 250/225 |
| 6,990,259 | B2 * | 1/2006 | Cunningham | B82Y 20/00 385/12 |
| 7,423,750 | B2 * | 9/2008 | Hoshizaki | G01N 21/645 250/458.1 |
| 7,595,881 | B2 | 9/2009 | Leonard | |
| 7,737,392 | B2 * | 6/2010 | Cunningham | B01L 3/5027 250/214.1 |
| 7,785,862 | B2 * | 8/2010 | Kim | B01L 3/5085 422/68.1 |
| 7,982,874 | B2 | 7/2011 | Kovalenko | |
| 8,101,897 | B2 * | 1/2012 | Schirr | G01N 21/6452 250/205 |
| 8,591,836 | B2 * | 11/2013 | Boege | B01L 3/50825 422/551 |
| 8,702,321 | B2 * | 4/2014 | Marple | G01J 3/0218 385/12 |
| 8,809,040 | B2 * | 8/2014 | King | G01N 21/6428 435/287.1 |
| 8,964,177 | B2 * | 2/2015 | Some | G01N 21/51 356/336 |
| 8,976,353 | B2 * | 3/2015 | Larkin | G01N 21/01 356/337 |
| 9,272,126 | B2 * | 3/2016 | Cunningham | A61M 39/08 |
| 9,341,564 | B2 * | 5/2016 | McNeil-Watson | B01L 3/5025 |
| 9,459,207 | B2 | 5/2016 | Hanlon | |
| 9,592,508 | B2 * | 3/2017 | Holmes | G01N 35/1072 |
| 9,594,870 | B2 * | 3/2017 | Hubbell | G06F 19/22 |
| 9,599,507 | B2 * | 3/2017 | Pawluczyk | G01J 3/0243 |
| 9,696,328 | B2 * | 7/2017 | Hansen | G01N 35/0099 |
| 9,778,329 | B2 * | 10/2017 | Heidmann | G01R 33/26 |
| 9,914,123 | B2 * | 3/2018 | Young | B01L 3/50851 |
| 2003/0026891 | A1 * | 2/2003 | Qiu | B01L 3/5085 427/58 |
| 2003/0048341 | A1 * | 3/2003 | Mutz | B01J 19/0046 506/12 |
| 2003/0077660 | A1 * | 4/2003 | Pien | B01L 3/5085 435/7.1 |
| 2003/0113766 | A1 * | 6/2003 | Pepper | B01L 3/5085 435/6.11 |
| 2004/0112978 | A1 * | 6/2004 | Reichel | B01L 3/0268 239/71 |
| 2008/0056950 | A1 * | 3/2008 | Weisbuch | G01N 21/6452 422/82.11 |
| 2008/0143828 | A1 * | 6/2008 | Mandrachia | G01N 21/51 348/82 |
| 2010/0032582 | A1 * | 2/2010 | Xia | G01J 3/02 250/458.1 |
| 2011/0059016 | A1 * | 3/2011 | Ramanujam | A61B 5/0059 424/9.1 |
| 2011/0067490 | A1 * | 3/2011 | Walsh | G01F 23/292 73/149 |
| 2011/0135244 | A1 * | 6/2011 | Marple | G01J 3/02 385/12 |
| 2011/0141466 | A1 * | 6/2011 | Magnusson | B01L 3/502715 356/319 |
| 2012/0075619 | A1 * | 3/2012 | Nieman | G01B 11/22 356/72 |
| 2014/0211204 | A1 * | 7/2014 | Stedtfeld | C12Q 1/686 356/244 |
| 2016/0077167 | A1 * | 3/2016 | Heidmann | G01N 24/10 324/304 |
| 2017/0104426 | A1 * | 4/2017 | Mills | H05H 1/24 |
| 2017/0301169 | A1 * | 10/2017 | Ghauch | G07D 7/1205 |
| 2017/0322133 | A1 * | 11/2017 | Trainer | G01J 3/0218 |

* cited by examiner excitation radiation - - - - - - - -
emission radiation ··············

HIGH THROUGHPUT METHOD AND APPARATUS FOR MEASURING MULTIPLE OPTICAL PROPERTIES OF A LIQUID SAMPLE

RELATED APPLICATIONS AND PATENTS

The following patents relate to the measurement of the physical properties of liquid samples in a multiwell plate and are hereby incorporated by reference:

U.S. Pat. No. 6,519,032 B1, S. C. Kuebler and J. Bennett, "Fiber optic apparatus and use thereof in combinatorial material science," issued Feb. 11, 2003.

U.S. Pat. No. 6,819,420 B2, S. C. Kuebler and J. Bennett, "Fiber optic apparatus and use thereof in combinatorial material science," issued Nov. 16, 2004.

U.S. Pat. No. 8,976,353 B2, M. I. Larkin, A. D. Hanlon, D. I. Some, R. J. Sleiman, D. N. Villalpando, "Mutiwell plate lid for improved optical measurements," issued Mar. 10, 2015.

U.S. Pat. No. 9,347,869 B2, M. I. Larkin, A. D. Hanlon, D. I. Some, R. J. Sleiman, D. N. Villalpando, "Mutiwell plate lid for improved optical measurements," issued May 24, 2016.

U.S. Pat. No. 9,459,207 B2, A. D. Hanlon, M. I. Larkin, "Method of characterizing interactions and screening for effectors," issued May 24, 2016.

U.S. Pat. No. 8,441,638 B2, H.-T. Hsieh, S. P. Trainoff, "Apparatus to measure particle mobility in solution with scattered and unscattered light," issued May 14, 2013.

BACKGROUND

Although the present disclosure will refer to particles throughout much of its specification, the invention includes more generally all classes of small particles including emulsions, macromolecules, viruses, nanoparticles, liposomes, macro-ions and any other solution constituents whose size may lie between a half and a few thousand nanometers. Thus whenever the terms "particle," "macromolecule," or "macro-ion" are used, it should be understood they include all of the aforementioned solution-borne objects. The present invention generally involves the characterization of particles and molecules in a liquid sample, and in particular the measurement of fluorescence and light scattering of samples contained within the wells of a multiwell plate. Methods capable of measuring samples directly in these multiwell plates are generally desirable given both the high-throughput nature of the measurements permitting the rapid screening of the individual samples, as well as the reduced sample volume requirements. Standard multiwell plates have 96, 384, or 1536 wells, each well is able to contain a different sample, and all wells, under common operational conditions, may be tested in a single data collection run. In addition, use of these plates obviates the laborious need to clean and dry individual scintillation vials after each measurement. These plates generally have very low volume wells, and commercially available multiwell plate based measurement instruments are capable of measurements from sample volumes of 1 μL or less. These tiny sample volumes are of great benefit when one has a limited amount of sample from which to make measurements, particularly when compared to the 300 μL or larger sized measurement volumes often required by other measurement techniques, such as flow-through fluorescence monitoring and flow-through multiangle light scattering (MALS). Other obvious benefits include the ability to automate the measurement of between 1 and over 1500 samples with little or no human intervention after the sample is prepared and introduced into the plate for analysis. Further labor saving benefits can be achieved, of course, by automated sample preparation robots such as the Freedom EVO® series produced by Tecan (Tecan Trading AG, Switzerland).

Multiwell plates can be used with various optical analysis techniques, most commonly absorbance measurements performed as light is scanned across a plate and the transmitted light is measured by a detector system placed on the opposite side of the plate to the incident light, permitting, thereby a measurement of the absorbance of light by the sample contained in each individual well as described, for example, by A. J. Russell and C. Calvert in U.S. Pat. No. 4,810,096 (Issued Mar. 7, 1989). Measurements of absorbance can enable a calculation of the concentration of the sample contained therein.

Light scattering measurements may also be performed in a multiwell plate as described by Kuebler, et. al., in U.S. Pat. No. 6,519,032 B1 (issued Feb. 11, 2003). In this technique a fine beam of light, generally produced by a laser, is directed to pass vertically through the sample contained in a single well (either from above or below), and scattered light is detected by a detector located beneath the sample well. The apparatus disclosed by Kuebler utilizes a technique generally referred to as dynamic light scattering (DLS) that is also known as quasi-elastic light scattering (QELS) and photon correlation spectroscopy (PCS). When in solution, sample particles are buffeted by the solvent molecules. This leads to a random motion of the particles called Brownian motion. As light scatters from the moving particles this random motion imparts a randomness to the phase of the scattered light, such that when the scattered light from two or more particles is combined a changing intensity of such scattered light due to interference effects will occur. The DLS measurement of the time-dependent fluctuations in the scattered light is achieved by a fast photon counter, generally connected by an optical fiber to collection optics located beneath the multiwell plate. The fluctuations are directly related to the rate of diffusion of the particles through the solvent. The fluctuations are then analyzed to yield diffusion coefficients and, from these, the hydrodynamic radii of the sample.

Another measurement of interest, which is a focus of the present invention, is the detection of fluorescence from particles contained within the liquid sample. In general fluorescence studies involve treating particles, such as chromosomes or proteins with a fluorescence tag or dye. The sample is then irradiated with an excitation light source, the protein tags are excited, causing electrons to rise to a higher energy state, when the electrons from the tagged proteins return to their ground state, they emit photons of a longer wavelength that can be captured by an optical detector, such as a photomultiplier tube (PMT), and analyzed, and thus the tagged proteins can be identified and characterized. Often the spectrum of the fluorescence is measured for even richer information content. Some molecules, most notably proteins, possess intrinsic fluorophores and can be excited with proper light sources. For example, UV light at 280 nm excites both tyrosine and tryptophan residues, while 295 nm light excites only fluorescence from tryptophan residues. Intrinsic protein fluorescence spectrum can be used to assess the tertiary protein structure as the fluorescence peak tends to red-shift as the residues are exposed to more polar environment. The measurement of protein free energy of unfolding can be determined by combining chemical denaturation, generally using urea or guanidine hydrochloride, with measurement of intrinsic fluorescence. The protein free energy of unfolding is an indicator of formulations stability.

Many systems have been developed to measure fluorescence of a sample materials, including directly from animal tissue, lab-on-a-chip technologies, or measuring fluorescence-labeled target molecules immobilized on a solid support. Significantly fewer developments have been concerned with fluorescence studies of liquid samples contained in a multiwell plate, although some patents have explored improvements to the collection of fluorescence data of samples contained therein. For example, U.S. Pat. No. 6,316,774 discloses a fluorimeter where light passes from the source through one of two optical fibers, the selection of which is controlled manually. These fibers permit illumination of the sample contained within a plate or cuvette either through the open top of the chamber or through the transparent closed bottom by reflecting the incoming light from the fiber with a concave, focusing mirror that directs the illumination to the sample chamber. Additional collecting mirrors and optics gather the emission radiation and direct it into optical fibers that carry the light to an optical shutter that permits passage from emitted light gathered either from above or below the sample plate.

Combined illumination and collection optics have been subject of other fluorimetry innovations. U.S. Patent Application No. US 2010/0032582 A1 (published Feb. 11, 2010) by H. Xia, et. al. utilizes a single optical fiber bundle comprising a central illumination fiber surrounded with a plurality of receiving fibers contained within a single bundle, and utilizing a single lens to direct the paths of both the excitation radiation to the sample and receipt of the emission radiation from the sample that is contained within a microfluidic channel. Similarly U.S. Pat. No. 4,678,326 (Issued Jul. 7, 1987) by H. Harjunmaa proposes a bundle of fibers with an emission fiber in the center and utilizing a pair of lenses to collimate excitation radiation through the bottom of cylindrical cuvette in order to avoid illumination of the cuvette walls by the incident light while maximizing the uniformity of illumination of the sample. The same lens configuration collects light emitted from the sample and directs it into a plurality of fibers arranged at specific radial distances surrounding the emission fiber selected so as to reject reflected light from the bottom surface of the cuvette.

In addition to these systems for measuring fluorescence from a multiwell plate, improvements to the optics and light collection and rejection systems have also been considered and are present in the prior art. For example U.S. Pat. No. 7,595,881 by S. W. Leonard, et. al, discloses a useful optical system wherein a shadow disc is placed within the path of emission radiation collected and directed, in free space, by a mirror located below the well plate. By careful positioning and alignment of the optical elements, the shadow disc absorbs light scattered by the meniscus of the sample cell, the remaining radiation is then focused with an aspheric lens onto a detector, improving the overall signal-to-noise of the collected light.

While all of these implementations offer significant improvements over fundamental fluorimeter systems, it is not until the present invention that a simplified system that maximizes the signal to noise ratio while minimizing stray light and permitting the high-throughput analysis enabled by multiwell plates has been possible.

A BRIEF DESCRIPTION OF THE SEVERAL VIEWS OF THE DRAWINGS

A DETAILED DESCRIPTION OF THE INVENTION

Figure 1:
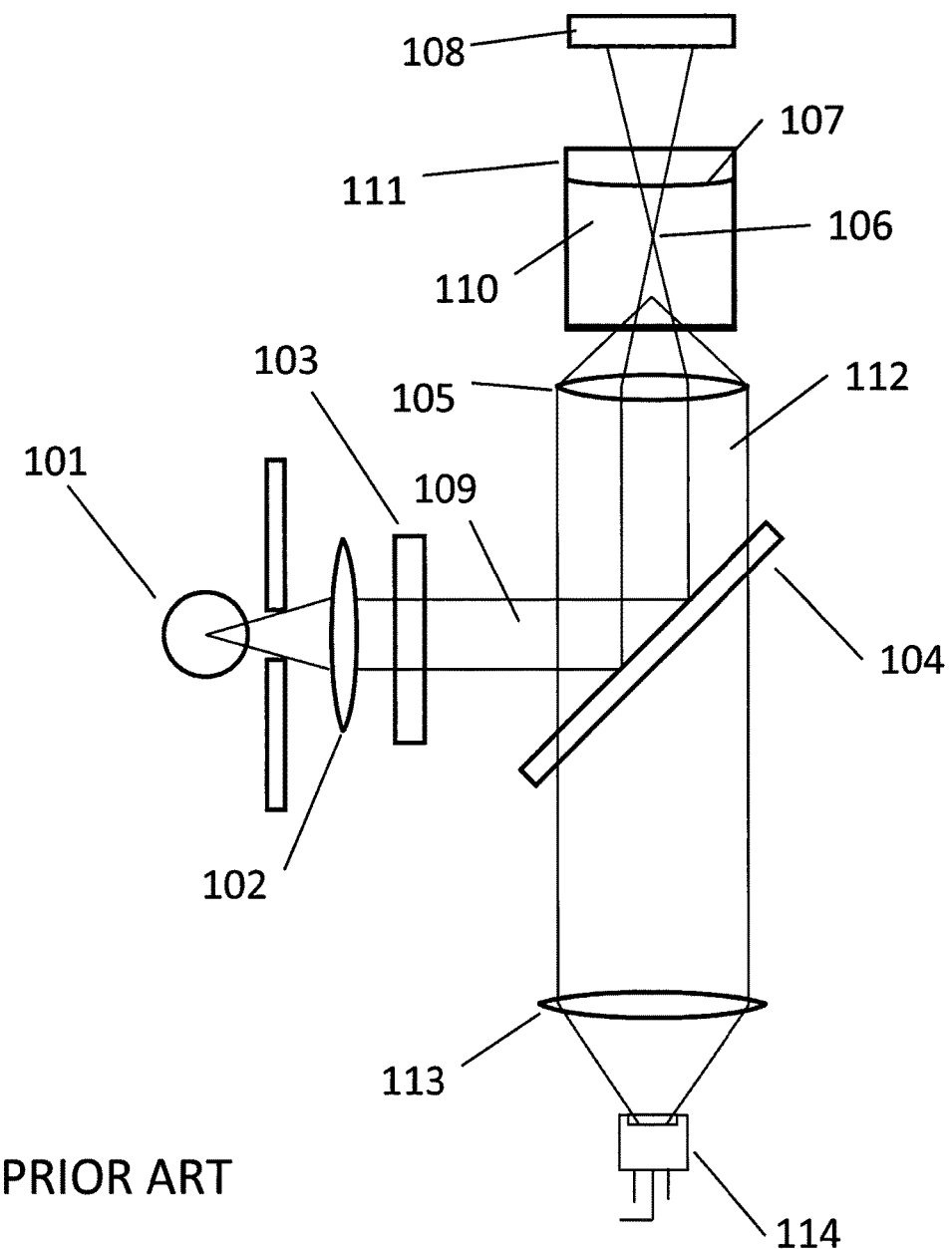
FIG. 1 shows a typical instrument for measuring fluorescence of a liquid sample contained within a cuvette.

FIG. 1 illustrates a conventional fluorimeter 100 for use with a liquid sample. An illumination source 101, which can either operate at a specifically chosen excitation wavelength, or over a range of possible wavelengths, generates a beam of light selected by an aperture and is generally collimated by a lens 102. The collimated beam may then pass through an optical filter 103 that permits the passage of a specifically selected excitation wavelength, $\lambda_1$, or range of wavelengths of radiation to pass there through. The excitation beam 109 is then directed towards the liquid sample 110 by a dichroic beam splitter 104 that reflects light at wavelength $\lambda_1$. The excitation beam then generally passes through a lens 105 that focuses the beam 109 to a point 106 somewhere within the liquid sample 110 contained within the sample vessel 111. The excitation beam 109 then exits the sample through the sample meniscus 107. The emerging beam may then intersect an optical detector 108 that measures the amount of light transmitted through the sample. As discussed above, the excitation beam may cause various molecules within the liquid sample to fluoresce at a wavelength $\lambda_2$, where $\lambda_1 < \lambda_2$. The fluorescent light that emerges from the bottom of the sample vessel 111 is collected and collimated by a lens 105 forming an emission beam 112. The emission beam 112 impinges upon the dichroic beam splitter 104 that has been selected to transmit, rather than reflect or absorb, at emission wavelength $\lambda_2$. The emission beam is then focused by a converging lens 113 which directs the beam towards a detector 114 which is generally a photomultiplier tube (PMT) or an avalanche photodiode (APD). It is also not uncommon for the dichroic beam splitter 104 to permit the passage of a percentage of light from the excitation beam 109 to pass there through and impinge upon a photodetector (not shown). When the intensity of light gathered by this detector is compared with the light gathered by the optical detector 108 located above the sample, it is possible to determine the absorption of light by the sample itself, broadening, thereby the utility of the system.

Figure 2:
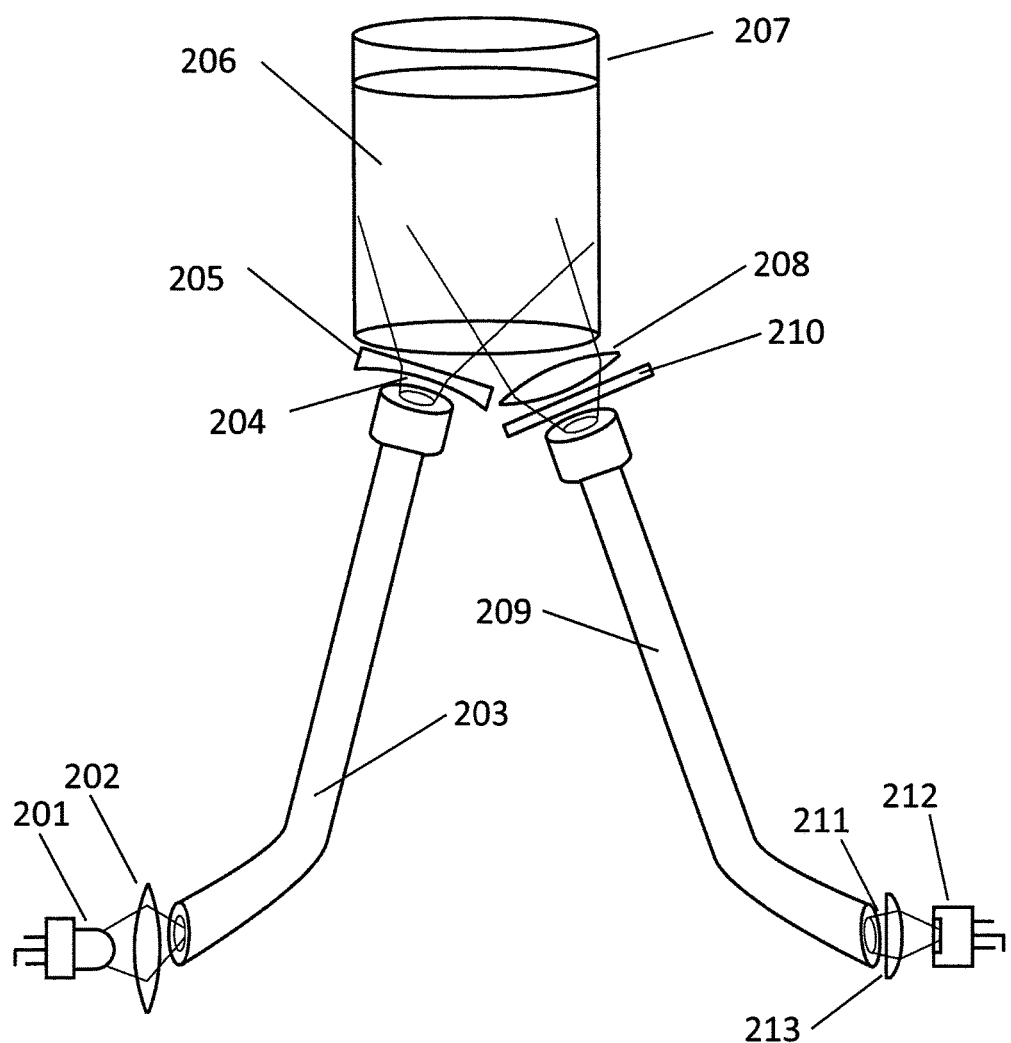
FIG. 2 illustrates a variation on the conventional fluorimeter shown in FIG. 1 wherein optical fibers are used to direct light to and collecting light from a liquid sample.

A variation on a conventional fluorimeter employs fiber optics for the delivery of excitation radiation as well as the collection of emission radiation, an example of such a system is illustrated in FIG. 2. The light source 101 of FIG. 1 can be replaced by a single wavelength light emitting diode (LED) or a UV laser source. In this case the optical filter 103 may be eliminated from the optical system as LEDs and laser sources generally operate at very narrow wavelength bands, and the LED or laser source would be selected to operate at the desired excitation wavelength. In this case, the LED source 201 is focused by a converging lens 202 onto one end of an optical fiber 203. In this specification we refer to this end of the fiber as the system end. By contrast the end of the fiber directly investigating the sample is referred to as the probe end. The excitation light passes through the fiber 203 and the emerging beam 204, at the probe end, may be expanded by a lens 205 such that the beam illuminates a large volume of the sample 206 contained in the vessel 207. Emission radiation leaving the vessel 207 can be gathered by a converging lens 208 and focused onto a second optical fiber 209 after passing through an optical filter 210 selected to allow only light of the expected emission wavelength to pass there through. The emission beam 211, after passing through the fiber 209 can be focused onto a detector 212 such as a PMT or APD by a converging lens 213. It is also possible to remove the attenuator, and rather than detect absolute luminosity, the spectrum of emitted radiation can be analyzed by replacing the detector 212 with a spectrometer. Further, the excitation source may employ multiple LEDs emitting light at multiple wavelengths, and then selecting from among those wavelengths one or more of the LEDs to illuminate the sample in order to optimize the determination of excitation wavelengths. Similarly, wide spectrum sources can be used in conjunction with filters which are selected to permit the passage of a single wavelength, the filtered beam is then focused on the excitation fiber 203 rather than using a narrow wavelength LED source.

Figure 3A:
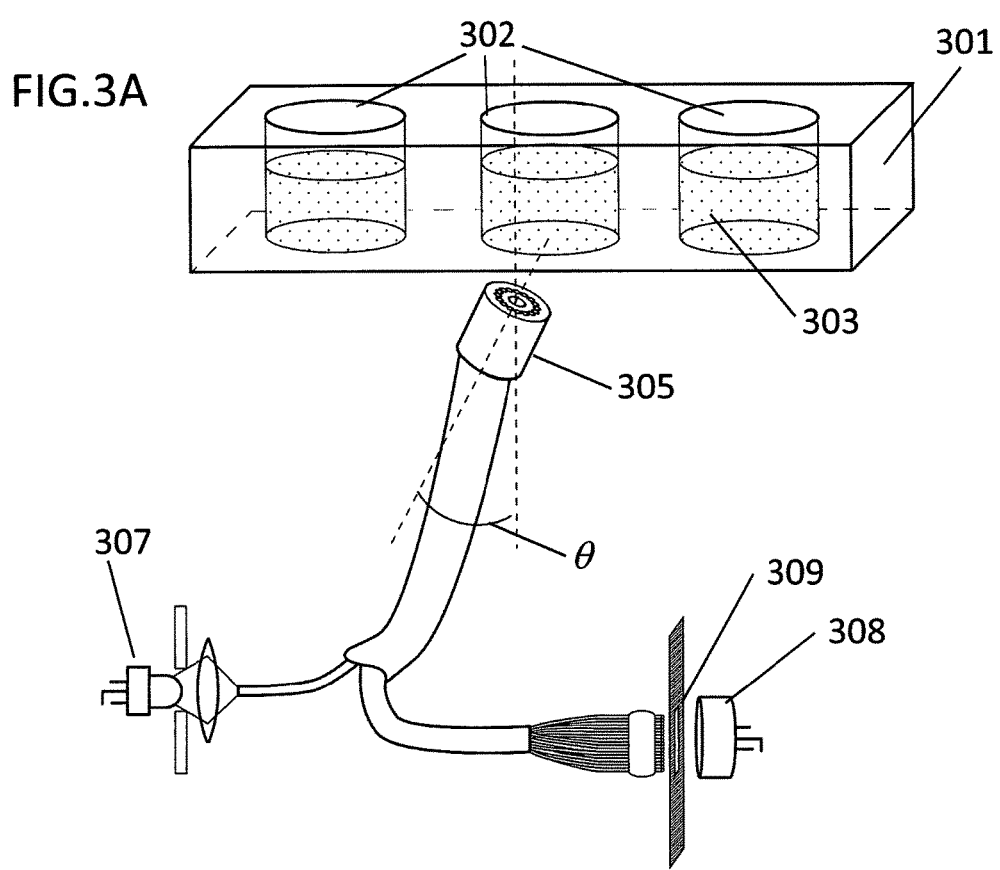
FIG. 3A shows an embodiment of the present invention wherein a single probe contains fibers that transmit the excitation beam and collect emission radiation from a sample contained in a multiwell plate.
Figure 3B:
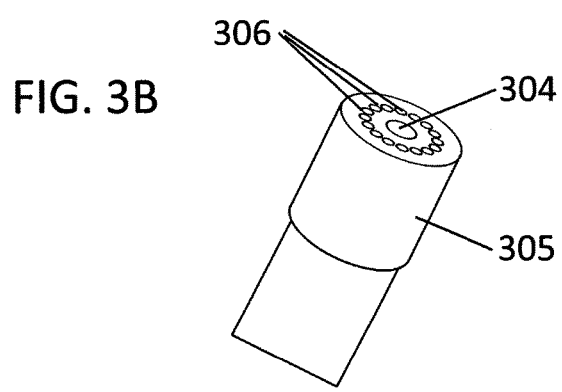
FIG. 3B exhibits a close up view of the probe barrel.

Several embodiments of the present invention comprise a novel means of transmitting excitation radiation to a liquid sample contained within a multiwell plate and receiving emission radiation therefrom. FIG. 3 illustrates one embodiment of the invention. The wells 302 of a multiwell plate 301 each contain a liquid sample 303 comprising fluorescently tagged or intrinsically fluorescent samples of interest. The bottom portion of the multiwell plate is transparent at least in a region directly below each of the wells. The remaining surfaces of the plate may be optically transparent, but in a preferred embodiment, the non-beam passing surfaces will absorb light at the wavelengths of either the excitation source or the emission wavelength or both. An optical probe 305 is located on a stage beneath the multiwell plate 301 where the stage may be a translation device capable of movement in at least X and Y directions relative to the multiwell plate positioned there above, allowing the probe 305 optical access to each of the wells individually by moving either the probe or the multiwell plate itself. Throughout this specification the terms "stage" and "translation device" indicate an object to which the probe or probes are mechanically attached. Neither term limits the invention to an embodiment wherein the probe/probes or multiwell plate is the moving element. The probe comprises a plurality of optical fibers wherein one or more of the fibers is an excitation radiation delivery vehicle capable of delivering a narrow-band light source, a broad-band light source, or a multitude of light sources. A plurality of remaining fibers collects emission radiation from the illuminated sample. In a preferred embodiment shown in FIG. 3, the excitation source is a LED with a center wavelength $\lambda_1$. The light from the LED is transmitted through a fiber 304 located at the center of the bundle of fibers which is contained in the probe barrel 305, as can be seen in FIG. 3B. A plurality of emission collection fibers 306 are arranged about the excitation fiber 304. The number of collection fibers 304 can range from one to any practical limit dictated by the size of the probe barrel 305 and possible orientations. In a preferred embodiment the number of excitation fibers is chosen to maximize the light gathering efficiency and detection signal to noise ratio. In contrast to the prior art discussed above, the present invention does not make use of any additional light gathering optics between the fibers themselves and bottom of the well plate. This conspicuous absence of transmission and gathering optics offers the novel advantages of minimizing the number of interfaces traversed by the excitation beam and emitted light. This drastically reduces stray light from excitation light scattering at the interfaces. Coupled with a slight tilt ($\theta=10°\sim20°$) between the probe barrel 305 and the plate bottom normal, the stray light from excitation source can be reduced to such a level that the excitation blocking filter at the detector is no longer necessary. As a result the excitation fiber 304 is able to illuminate the sample in a controlled and consistent manner as it moves from well to well. In addition each of the emission radiation receiving fibers collects based on the positioning of the fibers within the face of the barrel, not based on the optics of a light gathering objective lens. Of course, this novel probe also reduces cost and alignment time associated with an objective lens (or lenses) otherwise contained within the barrel of the probe or otherwise situated between the probe and the well plate itself.

In one embodiment of the invention, the excitation sources is a LED 307 operating at a wavelength selected so as to excite atoms of molecules contained within the sample. The light from the LED 307 is delivered at the probe end with the emission radiation gathering fibers 306 in the probe barrel 305. The fiber bundle is bifurcated with the illumination fiber or fibers coupled to the light sources and the emission fibers 306 splitting off from the bundle to be directed to a light sensitive detector or a spectrometer 308. In one preferred embodiment the emission gathering fibers on the system end are arranged into a linear array, permitting thereby the maximum amount of gathered emission light to pass through a linear slit 309 at the entrance of a detector such as a spectrometer 308.

Figure 4A:
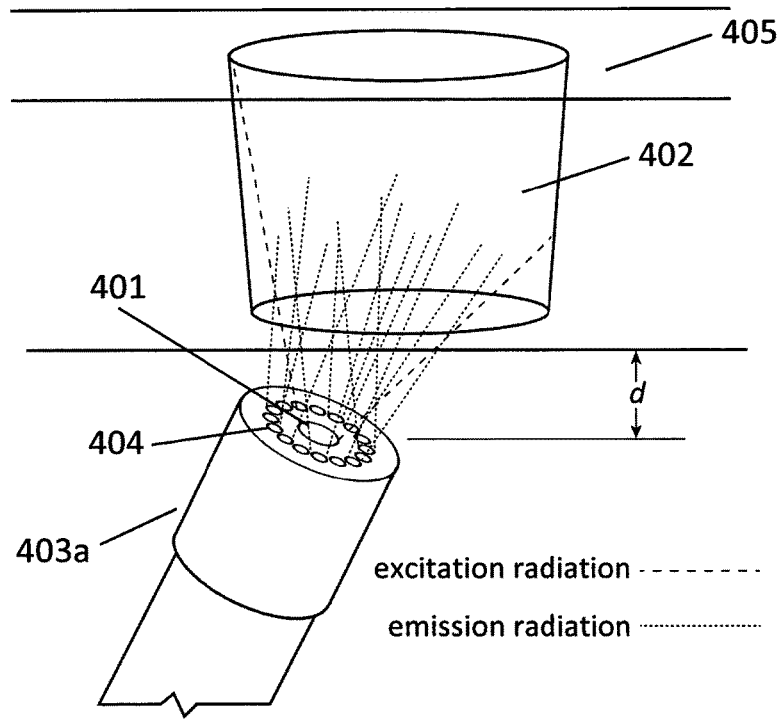
FIG. 4A is a detailed view of the excitation and emission radiation transmitted from and collected by the probe.
Figure 4B:
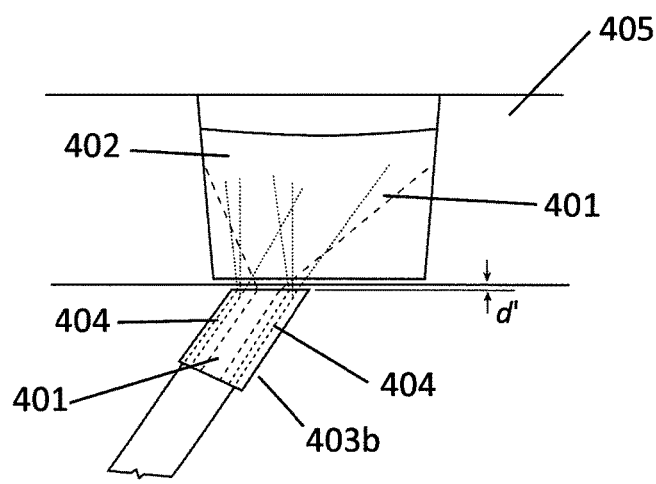
FIG. 4B shows a preferred embodiment of the probe barrel which is beveled such that the fluorescence excitation/probe barrel may be brought as close to the plate bottom as possible.

The probe barrel 305 containing the probe ends of both the excitation 304 and collection fibers 306 is positioned at an angle θ normal to the bottom of the plate. This configuration minimizes back reflection from the bottom surface of the well plate. FIG. 4A shows an excitation beam delivered by the excitation fiber 401 and emission from the sample 402 is collected by collection fibers 404. In a preferred embodiment of the invention, a cross section of which is shown if FIG. 4B, the barrel 403b is beveled and the contained fibers are both beveled and polished at an angle of around θ+90°, such that the flat surface of the barrel is essentially parallel to the bottom of the multiwell plate 405. This preferred embodiment enables both the probe to be placed much closer to the bottom of the multiwell plate 405, where distance d' between the face of the beveled barrel and the bottom of the multiwell plate is much smaller than the distance d between the plate and the center of the barrel 403a held at an angle, minimizing back-reflections from optical interfaces, particularly those that would be required if an objective lens were used to shape and direct radiation, as is the case in conventional systems. This novel beveled barrel also allows the fibers to collect radiation passing normal through the bottom of the sample well, as the faces of the fiber are polished flush to the beveled angle, and thus light exiting normal to the bottom face of the multiwell plate will pass directly into the probe.

Figure 5:
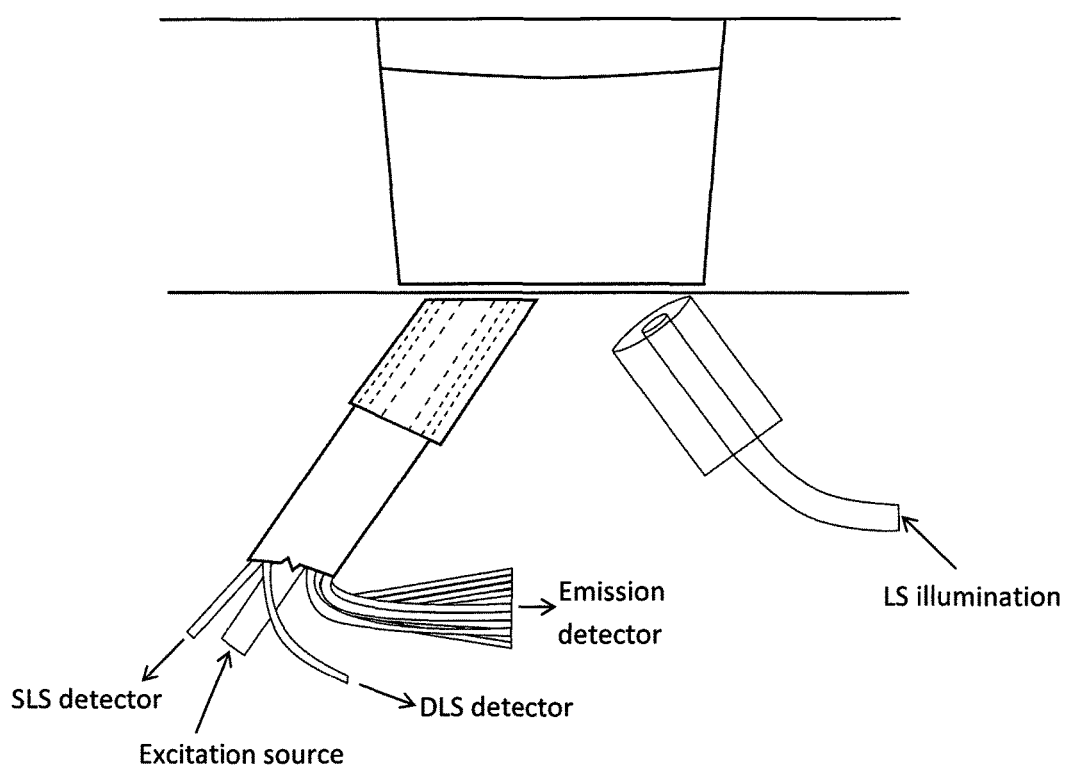
FIG. 5 shows a preferred embodiment of the invention wherein two fiber bundle probes act in concert to collect fluorescence and light scattering signals from the liquid sample located in the well of a multiwell plate.

In addition to the fluorescence detection discussed thus far in this disclosure, another embodiment of the invention enables the collection of light scattering data from liquid sample contained in the same multiwell plate. By using a second probe in conjunction with that discussed previously, one may combine fluorescence detection with both static light scattering (SLS) and dynamic light scattering (DLS) in a single measurement instrument, capable of making a plurality of measurements simultaneously or in succession from a multiwell plate, allowing a wealth of information to be acquired in a fraction of the time conventionally necessary in a high throughput system. As shown in FIG. 5, the beveled fluorescence probe of FIG. 4 may be accompanied by a separate optical fiber acting as an illumination source for light scattering measurements. In a preferred embodiment of the invention the light scattering illumination fiber will be a single-mode, polarization-maintaining fiber and the DLS detecting fiber can be a single-mode or multi-mode fiber. In another preferred embodiment of the invention, both the DLS and SLS fibers will have a diameter of approximately nine microns. Two of the fibers in the fluorescence probe bundle will serve as SLS and DLS collection and transmission vehicles, permitting thereby measurements of light scattering at a fixed angle from the incident beam.

In certain circumstances corrective optics may enhance SLS and DLS detection. While it is possible in some embodiments of the invention to attach corrective optics directly to the fibers to be utilized for light scattering purposes, it is perhaps simpler to employ a third probe dedicated to light scattering detection which may house separate fibers for the SLS and/or DLS detection. As such, another embodiment of the invention comprises the elements shown in FIG. 5 as well as a third probe housing containing corrective optics and one or more fibers coupled to the DLS and/or SLS detectors. In this embodiment the fluorescence probe may be dedicated completely to excitation and emission detection or may still utilize one or more fibers coupled to independent SLS or DLS detectors, permitting thereby light scattering data collected with and without corrective optics to be compared. In this embodiment the dedicated light scattering probe shares a single optical barrel and lens on one end and the system end is separated into the individual or groups of fibers, such as the "fan-out" fiber optic bundles produced by Thorlabs (Newton, N.J.). The three detector probes in these embodiments, namely the fluorescence probe, light scattering illumination probe, and light scattering detection probe may be rigidly coupled to each other by means of a movable stage such that they may investigate the same sample well of a multiwell plate simultaneously or with optical investigations being performed in series, without the need to move the stage to which the probes are rigidly coupled, or to move the multiwell plate relative to the stage. In another variation, fluorescence probe may be so positioned relative to the light scattering illumination probe and light scattering detection probe that the fluorescence probe measures fluorescence of one sample while the light scattering probes measure light scattering from a separate sample located within the same multiwell plate.

Under certain circumstances it may be required to adjust the height of the stage to which the probes are connected relative to the multiwell plate, therefore another variation enables the movement of the stage relative to the plate along the z-axis as well as the x-y axes. For example, consider a multiwell plate wherein very small amounts of sample are added to a plurality of wells, and therefore the well is only partially filled. It may be of interest to make a fluorescence measurement with the beveled fluorescence probe shown in FIG. 5 as close as possible to the bottom of the multiwell plate, but as the light scattering probe may be aligned such that it collects light scattered from the mid height of the well. In this case, this embodiment permits the positioning of the fluorescence probe very close to the multiwell plate for a fluorescence measurement, and then the stage may be moved along the z-axis away from the bottom of the plate, to allow the detection of light scattering from sample nearer the bottom of the well in order to avoid any noise associated with the meniscus of the liquid sample.

While much of this disclosure concerns the enablement of fluorescence detection from a liquid sample in a multiwell plate, another embodiment of the invention is that described above but absent the fluorescence probe. In this embodiment there are only two probes, one is the light scattering illumination source and the other houses corrective optics and two or more fibers, at least one of which is coupled to a DLS detector and at least one of which is coupled to an SLS detector.

Further, another embodiment of the invention permits the measurement of electrophoretic mobility of the liquid sample contained with a well by incorporating into the system a pair of electrodes, which may be either elements of a specialized well plate or elements of a plate lid that covers the plate, the electrodes connected thereto contacting the liquid sample. As discussed by Hsieh and Trainoff in U.S. Pat. No. 8,441,638 B2, "Apparatus to measure particle mobility in solution with scattered and unscattered light," (Issued May 14, 2013) (the '638 patent), the electrophoretic mobility is the directly measurable and most widely used quantity which characterizes the electrostatic properties of the molecules, or for that matter any other particles present, in such solutions. In this embodiment a voltage is applied across the electrodes, and charged particles within the sample migrate towards the oppositely charged electrode. The light scattering illumination beam is split prior to entry into the well into a sample beam and a reference beam. The sample beam passes through the liquid sample, but the reference beam does not, and is phase modulated by an external source, such as a piezo driven mirror as described in the '638 patent. Light scattered from the sample exposed to the electric field is collected by one or more of the collection fibers and recombined with the reference beam and the resulting beam is measured by a photodetector such photodiode. The signal from electrophoretic mobility detector is then analyzed to extract optical phase information, giving a first-principle measurement of the electrophoretic velocity of the macromolecules within the scattering volume.

As will be evident to those skilled in the arts of optical measurements from liquid samples, the benefits conveyed by the present invention are far reaching, and there are many obvious variations of the methods of the invention that do not depart from the fundamental elements that disclosed herein; all such variations are but obvious implementations of the described invention and are included by reference to our claims, that follow.

The invention claimed is:

1. An apparatus comprising:
 a multiwell plate comprising at least one vessel configured to contain a suspended liquid sample,
  wherein the at least one vessel comprises a transparent bottom surface;
 a primary optical fiber bundle comprising a probe end and a system end,
  wherein the primary optical fiber bundle comprises
   at least one illumination fiber optically coupled to an excitation radiation source on the system end of the primary optical fiber bundle and positioned to illuminate the suspended liquid sample on the probe end of the primary optical fiber bundle, and a plurality of collection fibers positioned, on the probe end of the primary optical fiber bundle, to collect radiation from the liquid sample illuminated by the at least one illumination fiber and optically coupled, on the system end of the primary optical fiber bundle, to at least one detector;

a translation device coupled to the probe end of the primary optical fiber bundle, wherein the translation device is configured to provide relative motion between the probe end of the primary optical fiber bundle and the transparent bottom surface;

wherein the plurality of collection fibers are arranged concentrically about the at least one illumination fiber on the probe end of the primary optical fiber bundle;

wherein the probe end of the primary optical fiber bundle is positioned at an angle to the bottom surface;

wherein the probe end of the primary optical fiber bundle is beveled, wherein the at least one illumination fiber is beveled, and wherein the plurality of collection fibers is beveled, such that a flat surface of the probe end of the primary optical fiber bundle is parallel to the bottom surface;

wherein the multiwell plate is stationary and the translation device is configured to move the probe end of the primary optical fiber bundle relative to the multiwell plate; and a secondary illumination optical fiber bundle mechanically coupled to the translation device, wherein the secondary illumination optical fiber bundle comprises a probe end and a system end, wherein the system end of the secondary illumination optical fiber bundle is optically coupled to a light scattering illumination source, wherein the primary optical fiber bundle is distinct from the secondary illumination optical fiber bundle, wherein the translation device is configured to move simultaneously the primary optical fiber bundle and the secondary illumination optical fiber bundle to a position under the at least one well.

2. The apparatus of claim 1
wherein the plurality of collection fibers, on the system end of the primary optical fiber bundle, are arranged in a linear array, and
further comprising a linear slit located between the linear array and the at least one detector.

3. The apparatus of claim 1 further comprising a light scattering detection optical fiber bundle mechanically coupled to the translation device,
wherein the light scattering detection optical fiber bundle comprises at least one optical fiber comprising a probe end and a system end,
wherein the at least one optical fiber of the light scattering detection optical fiber bundle is oriented so as to be able to collect light scattered from the sample by at least one of the light scattering illumination source and the excitation radiation source on the probe end of the at least one optical fiber and is optically coupled to at least one light scattering detector on the system end of the at least one optical fiber.

4. The apparatus of claim 1 wherein the light scattering illumination source is a laser.

5. The apparatus of claim 1 wherein at least one optical fiber of the primary optical fiber bundle is optically coupled on the system end of the primary optical fiber bundle to a static light scattering detector.

6. The apparatus of claim 1 wherein at least one optical fiber of the primary optical fiber bundle is optically coupled on the system end of the primary optical fiber bundle to a dynamic light scattering detector.

7. The apparatus of claim 1 wherein the at least one detector is a fluorescence spectrometer.

8. The apparatus of claim 1 wherein the excitation radiation source is a variable wavelength source.

9. The apparatus of claim 1 wherein the excitation source is a light emitting diode.

10. The apparatus of claim 1 wherein the secondary illumination optical fiber bundle is a single-mode, polarization-maintaining fiber.

* * * * *